United States Patent
Wu

(10) Patent No.: US 11,111,660 B2
(45) Date of Patent: Sep. 7, 2021

(54) SMART CONTROL SYSTEM AND METHOD IMPLEMENTED IN BATHROOM

(71) Applicant: Chiun Mai Communication Systems, Inc., New Taipei (TW)

(72) Inventor: Kuo-Wei Wu, New Taipei (TW)

(73) Assignee: Chiun Mai Communication Systems, Inc., New Taipei (TW)

( * ) Notice: Subject to any disclaimer, the term of this patent is extended or adjusted under 35 U.S.C. 154(b) by 0 days.

(21) Appl. No.: 16/516,337

(22) Filed: Jul. 19, 2019

(65) Prior Publication Data

US 2020/0032497 A1 Jan. 30, 2020

(30) Foreign Application Priority Data

Jul. 25, 2018 (CN) .......................... 201810823022.6

(51) Int. Cl.
*A47K 10/32* (2006.01)
*E03D 9/00* (2006.01)
*G01N 33/00* (2006.01)
*H04L 12/28* (2006.01)

(52) U.S. Cl.
CPC .............. *E03D 9/002* (2013.01); *A47K 10/32* (2013.01); *E03D 9/005* (2013.01); *E03D 9/007* (2013.01); *G01N 33/0073* (2013.01); *H04L 12/282* (2013.01); *A47K 2010/3226* (2013.01); *G05B 2219/2642* (2013.01)

(58) Field of Classification Search
None
See application file for complete search history.

(56) References Cited

U.S. PATENT DOCUMENTS

| 6,360,181 B1* | 3/2002 | Gemmell | G07F 9/002 702/128 |
| 2001/0032353 A1* | 10/2001 | Contadini | E03D 9/007 4/222 |
| 2002/0007510 A1* | 1/2002 | Mann | E03C 1/057 4/300 |
| 2005/0171634 A1* | 8/2005 | York | G16H 40/20 700/231 |

(Continued)

FOREIGN PATENT DOCUMENTS

| CN | 104635525 | 5/2015 |
| CN | 106063687 | 11/2016 |

(Continued)

*Primary Examiner* — Jennifer L Norton
(74) *Attorney, Agent, or Firm* — ScienBiziP, P.C.

(57) ABSTRACT

A smart control system for monitoring a bathroom includes a server, a smart toilet, a smart door handle, and a roller. The smart toilet includes a first sensor configured to detect whether the smart toilet is clean and send a first detection result to the server. The smart door handle includes a second sensor configured to detect whether the door of the bathroom is in an open state or a closed state and send a second detection result to the server. The roller includes a third sensor configured to detect a usage of the toilet paper on the roller and send a third detection result to the server. The server analyzes the first detection result, the second detection result, and the third detection result to obtain an analysis result. The server performs corresponding operations according to the analysis result.

9 Claims, 7 Drawing Sheets

(56) References Cited

U.S. PATENT DOCUMENTS

| | | | | |
|---|---|---|---|---|
| 2013/0124247 A1* | 5/2013 | Yenni | ............ | G06Q 10/087 |
| | | | | 705/7.15 |
| 2017/0372589 A1* | 12/2017 | Becker | ............ | G16H 40/20 |
| 2020/0217057 A1* | 7/2020 | Spiro | ............ | G08B 21/245 |
| 2020/0250774 A1* | 8/2020 | Agarwal | ............ | H04Q 9/00 |
| 2020/0392710 A1* | 12/2020 | Saruta | ............ | E03D 11/00 |

FOREIGN PATENT DOCUMENTS

| | | |
|---|---|---|
| CN | 106063687 A | 11/2016 |
| CN | 206460291 U | 9/2017 |
| CN | 107945432 A | 4/2018 |

\* cited by examiner

SMART CONTROL SYSTEM AND METHOD IMPLEMENTED IN BATHROOM

FIELD

The subject matter herein generally relates to smart control systems, and more particularly to a smart control system for monitoring a bathroom.

BACKGROUND

Public bathrooms may be occupied or may run out of toilet paper. Currently, there is no known method to know which bathrooms are available for use and which bathrooms have an adequate amount of toilet paper.

BRIEF DESCRIPTION OF THE DRAWINGS

Implementations of the present disclosure will now be described, by way of embodiments, with reference to the attached figures.

DETAILED DESCRIPTION

Figure 1:
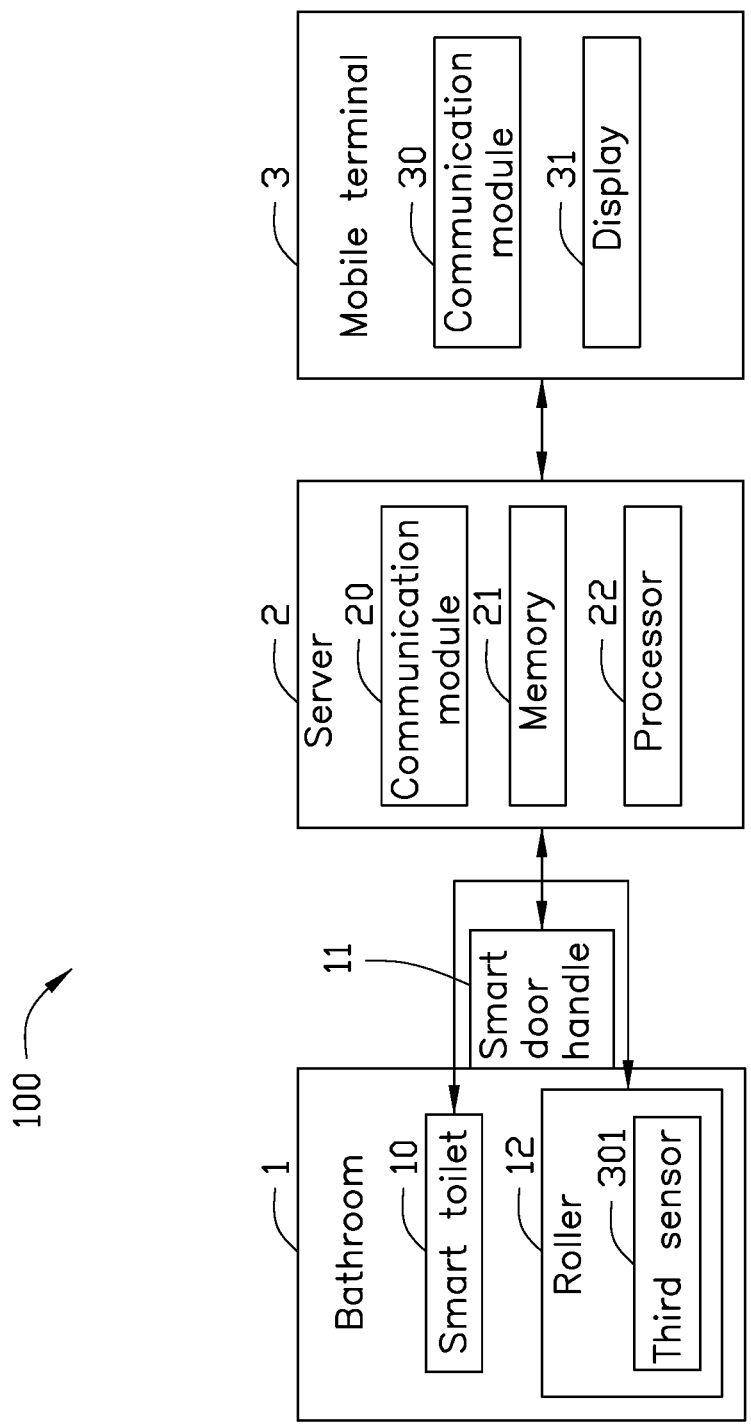
FIG. 1 is a block diagram of an embodiment of an application environment of a smart control system for monitoring a bathroom.

It will be appreciated that for simplicity and clarity of illustration, where appropriate, reference numerals have been repeated among the different figures to indicate corresponding or analogous elements. Additionally, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "comprising" means "including, but not necessarily limited to"; it specifically indicates open-ended inclusion or membership in a so-described combination, group, series and the like.

FIG. 1 shows a diagram of an application environment of a smart control system 100 for monitoring a bathroom 1. The smart control system 100 is applied in an application environment including the bathroom 1, a server 2, and a mobile terminal 3. The bathroom 1 includes, but is not limited to, a smart toilet 10, a smart door handle 11, and a roller 12. In one embodiment, the smart toilet 10 and the roller 12 are installed in the bathroom 1, and the smart door handle 11 is installed on an outer side of a door of the bathroom 1. The smart toilet 10, the smart door handle 11, and the roller 12 are communicatively coupled to the server 2. FIG. 1 only shows one bathroom 1, but in other embodiments there can be a plurality of bathrooms 1 in the smart control system 100.

In one embodiment, the server 2 includes, but is not limited to, a communication module 20, a memory 21, and a processor 22. The communication module 20 and the memory 21 are electrically coupled to the processor 22. The server 2 is communicatively coupled to the mobile terminal 3 through a network via the communication module 20. When a user needs to use the bathroom 1, the bathroom 1 that is not occupied, cleaned, and has sufficient toilet paper can be found through a message of the smart control system 100.

In one embodiment, the communication module 20 can be a communication chip complying with the corresponding network. The network can be, but is not limited to, a wireless network including WIFI and BLUETOOTH, or a broadcasting network. The memory 21 is used to store software programs and data installed in the server 2. The memory 21 may be an internal storage unit of the server 2, such as a hard disk or a memory of the server 2. In other embodiments, the memory 21 may also be an external storage device of the server 2, such as a plug-in hard disk, a smart memory card (SMC), and a secure digital (SD) card or flash card equipped on the server 2. The processor 22 can be a central processing unit, a microprocessor, or other data processing chip.

In one embodiment, the mobile terminal 3 includes, but is not limited to, a communication module 30 and a display 31. The communication module 30 and the display 31 are electrically coupled together. The communication module 30 can be a communication chip configured to provide wired or wireless network communication for the mobile terminal 3. In one embodiment, the mobile terminal 3 is communicatively coupled to the server 2 via a wireless network provided by the communication module 30. The display 31 can be a liquid crystal display (LCD) or an organic light-emitting diode (OLED) display. The display 31 is configured to display message information and other graphic information. The display 31 can have a touch function. The mobile terminal 3 can be a smart phone, a tablet, or a wearable device such as a wearable watch, a wristband, or the like.

Figure 2:
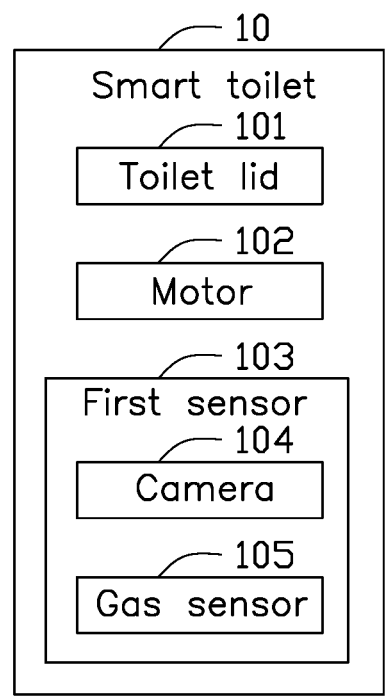
FIG. 2 is a block diagram of a smart toilet of the smart control system.
Figure 3:
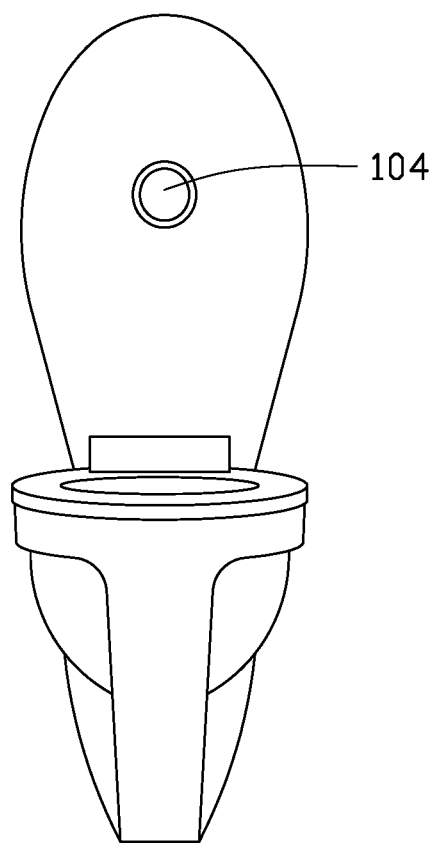
FIG. 3 is a diagram of the smart toilet.

Referring to FIGS. 2-3, in one embodiment, the smart toilet 10 includes, but is not limited to, a toilet lid 101, a motor 102, and a first sensor 103. The motor 102 is communicatively coupled to the server 2, and the motor 102 can control opening and closing of the toilet lid 101. The first sensor 103 is coupled to the server 2, and the first sensor 103 sends a first detection result to the server 2. The server 2 analyzes the first detection result to determine whether the smart toilet 10 is currently clean.

The first sensor 103 includes a camera 104 and a gas sensor 105. The camera 104 may be an infrared camera for capturing an image inside the smart toilet 10 and transmitting the image to the server 2. The server 2 compares the image captured in the smart toilet 10 with a pre-stored image of the smart toilet 10 in a clean state to analyze whether the smart toilet 10 is currently clean.

When an image similarity between the captured image inside the smart toilet 10 and the pre-stored image is greater than or equal to a preset value, the smart toilet 10 is in a clean state, and the server 2 sends a message to the mobile terminal 3 carried by a user indicating that the smart toilet 10 is currently in a clean state so that a user carrying the mobile terminal 3 can know the smart toilet 10 is ready to use. When the image similarity between the captured image inside the smart toilet 10 and the pre-stored image is less than the preset value, the smart toilet 10 is not in a clean state, and the server 2 sends a message to the mobile terminal 3 carried by cleaning personnel indicating that the smart toilet 10 is currently not in the clean state so that cleaning personnel carrying the mobile terminal 3 can promptly clean the smart toilet 10. If the smart toilet 10 is currently in an unclean state, the server 2 can also control the smart toilet 10 to automatically flush and deodorize. In one embodiment, the server 2 can send a control signal to the smart toilet 10 to control the smart toilet 10 to perform automatic flushing and deodorization (such as initiating an automatic spray of fragrance installed in the bathroom 1).

It should be understood that in order to protect user privacy through the camera 104, in one embodiment, the camera 104 is mounted inside the toilet lid 101 (as shown in FIG. 3), and the camera 104 can be shielded by a lens cover covering the camera 104 when the smart toilet 10 is in use. In one embodiment, the motor 102 can control the opening and closing of the toilet lid 101. A time duration required for the toilet lid 101 to open to a preset angle is set as a first time duration, and the server 2 controls the lens cover to shield the camera 104 after the first time duration to protect user privacy.

It should be understood that the preset angle is an angle between the toilet lid 101 and a toilet seat. The motor 102 can control a speed at which the toilet lid 101 is opened, so that the first time duration required for the toilet lid 101 to open to the preset angle can be calculated. When the angle between the toilet lid 101 and the toilet seat is greater than or equal to the preset angle, the server 2 controls the lens cover to shield the camera 104. When the angle between the toilet lid 101 and the toilet seat is less than the preset angle, the server 2 controls the lens cover to not shield the camera 104.

The gas sensor 105 is configured to detect a type and concentration of gas in the bathroom 1. In one embodiment, the gas sensor 105 can be used to detect gases including, but not limited to, hydrogen sulfide, ammonia, methyl mercaptan, hydrazine, methane, and ethane to indicate an odor in the bathroom 1. The gas sensor 105 transmits the detected type and concentration information of the gas in the bathroom 1 to the server 2, and the server 2 analyzes whether the toilet 10 is clean according to the type and concentration of the gas. In one embodiment, when the gas sensor 105 detects that a concentration of any type of gas is greater than or equal to a preset value, the server 2 determines that the toilet 10 is not clean. When the gas sensor 105 detects that a concentration of all detected types of gas is less than the preset value, the server 2 determines that the toilet 10 is clean. The gas sensor 105 may be a semiconductor gas sensor, an infrared absorption gas sensor, an electrochemical sensor, or other intelligent gas sensor.

Figure 4:
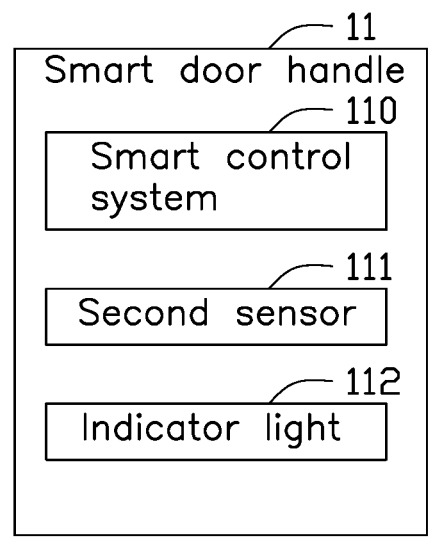
FIG. 4 is a block diagram of a smart door handle of the smart control system.

Referring to FIG. 4, in one embodiment, the smart door handle 11 includes a switch 110, a second sensor 111, and an indicator light 112. The second sensor 111 is configured to detect whether the switch 110 is turned off, generate a second detection result, and send the second detection result to the server 2, so as to detect whether a door of the bathroom 1 is closed. In one embodiment, the second sensor 111 may be a proximity sensor mounted in the switch 110. When the door of the bathroom 1 is closed, the switch 110 is in a closed state, at which time the proximity sensor is blocked by the switch 110, and a distance detected by the proximity sensor is less than or equal to a preset distance. When the door is opened, the switch 110 is in an open state, and the proximity sensor is not blocked by the switch 110, so that the distance detected by the proximity sensor is greater than the preset distance. The second sensor 111 sends the detected distance to the server 2, and the server 2 compares the detected distance with the preset distance to determine whether the door of the bathroom 1 is closed.

When the server 2 determines that the door of the bathroom 1 is in the closed state, the server 2 controls the indicator light 112 to display a red light to indicate that the bathroom 1 is currently occupied. When the server 2 determines that the door of the bathroom 1 is in the open state, the server 2 controls the indicator light 112 to display a first color, such as a green light, to indicate that the bathroom 1 is not currently occupied.

In one embodiment, the indicator light 112 of the smart door handle 11 can also indicate a usage of the toilet paper on the roller 12 in the bathroom 1. When it is detected that the toilet paper on the roller 12 is sufficient and the bathroom 1 is not currently occupied, the indicator light 112 on the smart door handle 11 displays a green light to indicate that the bathroom 1 is not occupied with confidence. When the toilet paper on the roller 12 is less than sufficient and the bathroom 1 is not currently occupied, the indicator light 112 on the smart door handle 11 displays a second color, such as a yellow light, to indicate that the bathroom 1 is not occupied, but the toilet paper is insufficient. When the bathroom 1 is currently occupied, regardless of whether the toilet paper in the bathroom 1 is sufficient, the indicator light 112 on the smart door handle 11 displays a third color, such as a red light, to indicate that the bathroom 1 is currently occupied.

Figure 5:
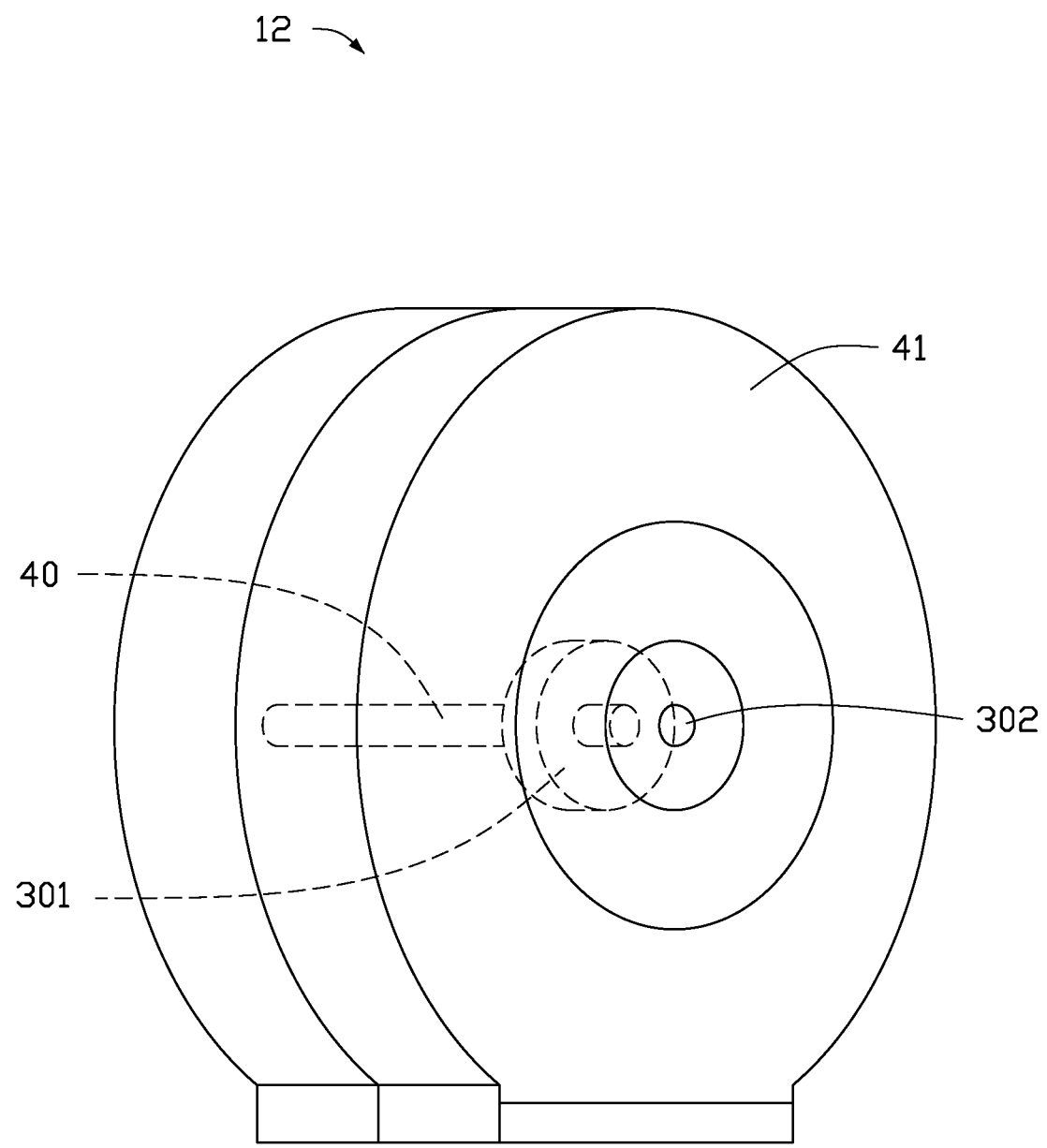
FIG. 5 is a diagram of a first embodiment of a roller of the smart control system.

Referring to FIG. 5, in one embodiment when the toilet paper is a jumbo roll of toilet paper, the roller 12 includes a stationary shaft 40 and a housing 41. The stationary shaft 40 can pass through a center hole of the jumbo roll of toilet paper, so that the toilet paper can be mounted on the stationary shaft 40. The housing 41 defines an inner cavity, and the stationary shaft 40 and the toilet paper are received in the inner cavity. The roller 12 further includes a third sensor 301 and an indicator light 302. The third sensor 301 is configured to detect the usage of the toilet paper on the roller 12 and send a third detection result to the server 2. The third sensor 301 can be a weight sensor or a proximity sensor. The weight sensor is located on the stationary shaft 40 for detecting a weight of the toilet paper. The weight sensor transmits the detected weight of the toilet paper to the server 2, and the server 2 controls the indicator light 302 to indicate the usage of the toilet paper according to the detected weight of the toilet paper.

In one embodiment, when the weight of the toilet paper is within a first preset weight range, the indicator light 302 displays a first color, such as a green color, indicating that the toilet paper on the roller 12 is sufficient. When the weight of the toilet paper is within a second preset weight range, the indicator light 302 displays a second color, such as a yellow color, indicating that the toilet paper on the roller 12 is less than sufficient. When the weight of the toilet paper is within a third preset weight range, the indicator light 302 displays a third color, such as a red color, indicating that there is no toilet paper on the roller 12. It should be understood that the first preset weight range is greater than the second preset weight range, and the second preset weight range is greater than the third preset weight range.

Figure 6:
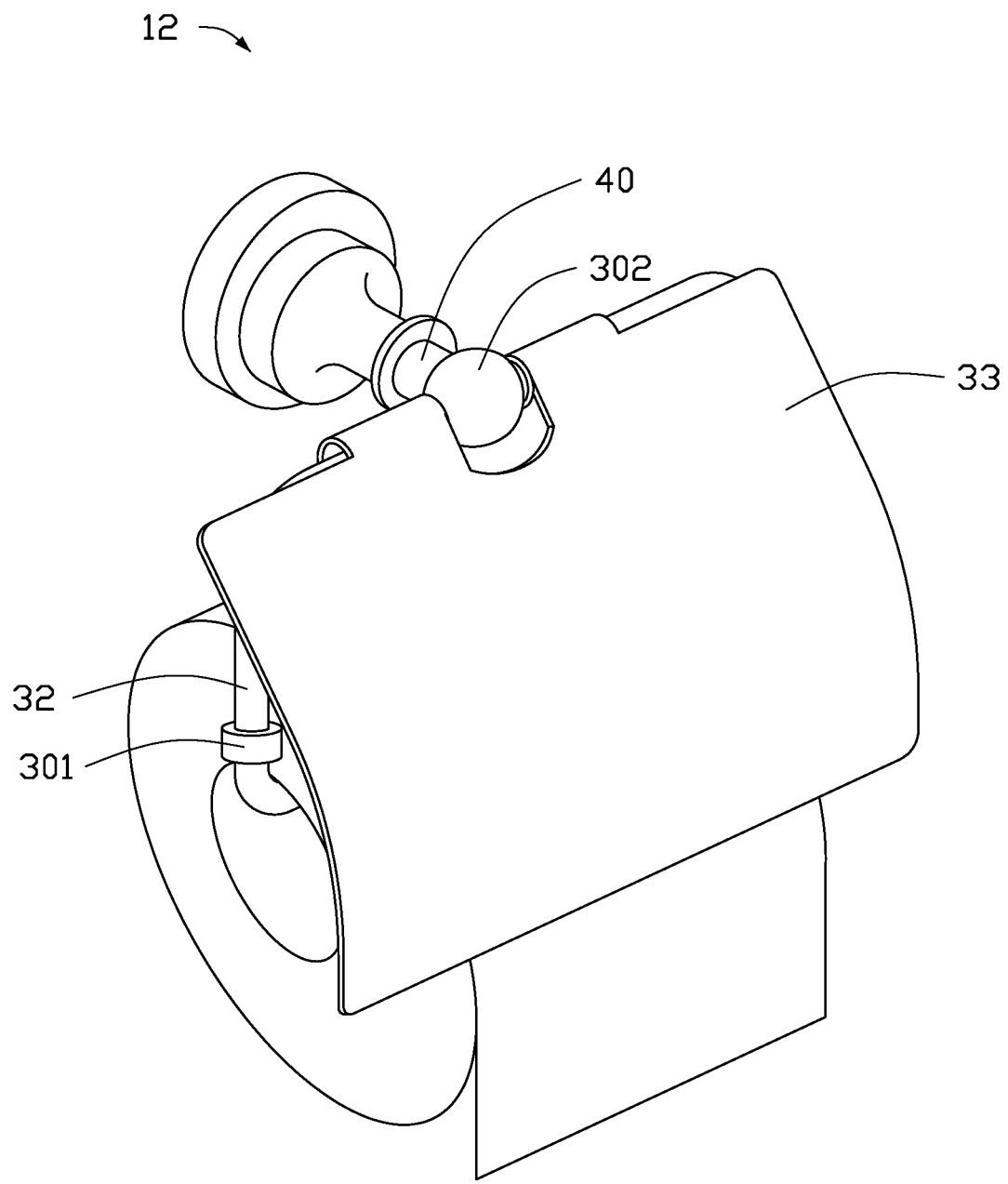
FIG. 6 is a diagram of a second embodiment of a roller of the smart control system.

As shown in FIG. 6, in another embodiment, when the toilet paper is a roll of toilet paper, the roller 12 includes a wall-mounted holding portion 40, a roller holding portion 32, and a cover plate 33. One end of the holding portion 40 is fixed to a stationary object (such as a wall). The roller holding portion 32 is coupled to another end of the holding portion 40. The cover plate 33 is rotationally mounted on one end of the roller holding portion 32 coupled to the holding portion 40. Another end of the roller holding portion 32 passes through a central hole of the roll of toilet paper to mount the toilet paper. In one embodiment, the roller 12 further includes a proximity sensor and an indicator light 302. The proximity sensor is located on the roller holding portion 32 for measuring a distance between the roller holding portion 32 and the cover plate 33. The proximity sensor sends the detected distance between the roller holding portion 32 and the cover plate 33 to the server 2, and the server 2 controls the indicator light 302 to indicate the usage of the toilet paper according to the detected distance between the roller holding portion 32 and the cover plate 33.

In one embodiment, when the distance between the roller holding portion 32 and the cover plate 33 is within a first preset distance range, the amount of toilet paper on the roller 12 is sufficient, and the indicator light 302 displays a first colored light, such as a green light. When the distance between the roller holding portion 32 and the cover plate 33 is within a second preset distance range, the amount of toilet paper on the roller 12 is less sufficient, and the indicator light 302 displays a second colored light, such as a yellow light. When the distance between the roller holding portion 32 and the cover plate 33 is within a third preset distance range, the roller 12 has no toilet paper, and the indicator light 302 displays a third colored light, such as a red light at this time. It should be understood that the first preset distance range is greater than the second preset distance range, and the second preset distance range is greater than the third preset distance range.

In another embodiment, the amount of toilet paper on the roller 12 can be determined according to a total length of the toilet paper on an inner tube of the toilet paper and an inner diameter of the inner tube. A number of times of the inner tube of the toilet paper rolling is detected when the toilet paper is pulled off the roller 12. The number of times of the inner tube rolling corresponds to the length of toilet paper used, which determines the amount of toilet paper remaining.

Figure 7:
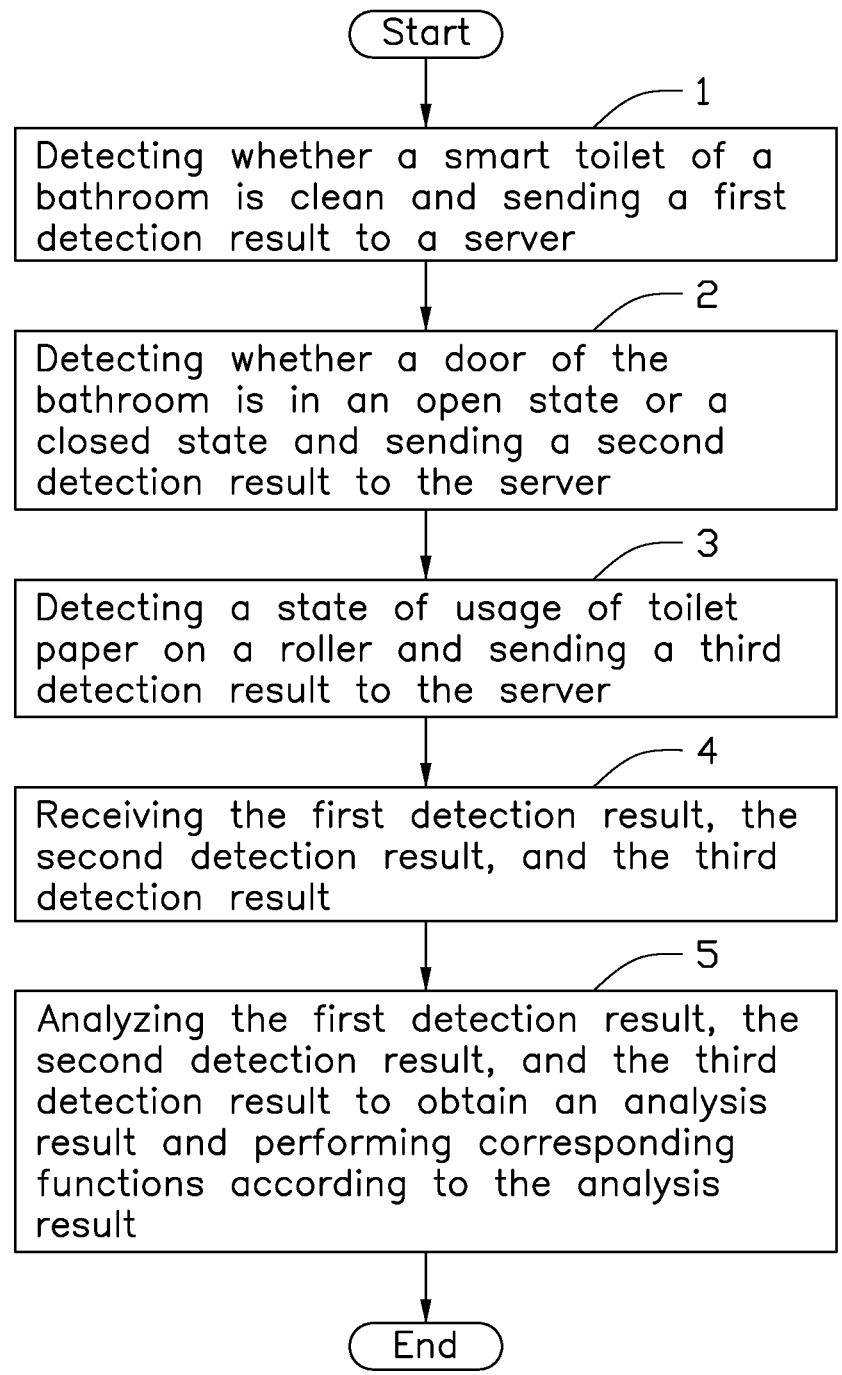
FIG. 7 is a flowchart of a smart control method for monitoring a bathroom.

FIG. 7 is a flowchart of a smart control method. The order of the blocks in the flowchart may be changed according to different requirements, and some blocks may be omitted or combined.

At block S1, the first sensor 103 detects whether the smart toilet 10 is clean and sends the first detection result to the server 2.

The first sensor 103 includes a camera 104 and a gas sensor 105.

The camera 104 may be an infrared camera for capturing an image inside the smart toilet 10 and transmitting the image to the server 2. The server 2 compares the image captured in the smart toilet 10 with a pre-stored image of the smart toilet 10 in a clean state to analyze whether the smart toilet 10 is currently clean.

When an image similarity between the captured image inside the smart toilet 10 and the pre-stored image is greater than or equal to a preset value, the smart toilet 10 is in a clean state, and the server 2 sends a message to the mobile terminal 3 carried by a user indicating that the smart toilet 10 is currently in a clean state so that a user carrying the mobile terminal 3 can know to use the smart toilet 10. When the image similarity between the captured image inside the smart toilet 10 and the pre-stored image is less than the preset value, the smart toilet 10 is not in a clean state, and the server 2 sends a message to the mobile terminal 3 carried by cleaning personnel indicating that the smart toilet 10 is currently not in the clean state so that cleaning personnel carrying the mobile terminal 3 can promptly clean the smart toilet 10. If the smart toilet 10 is currently in an unclean state, the server 2 can also control the smart toilet 10 to automatically flush and deodorize. In one embodiment, the server 2 can send a control signal to the smart toilet 10 to control the smart toilet 10 to perform automatic flushing and deodorization (such as initiating an automatic spray of fragrance installed in the bathroom 1).

The gas sensor 105 is configured to detect a type and concentration of gas in the bathroom 1. In one embodiment, the gas sensor 105 can be used to detect gases including, but not limited to, hydrogen sulfide, ammonia, methyl mercaptan, hydrazine, methane, and ethane to indicate an odor in the bathroom 1. The gas sensor 105 transmits the detected type and concentration information of the gas in the bathroom 1 to the server 2, and the server 2 analyzes whether the bathroom 1 is clean according to the type and concentration of the gas. In one embodiment, when the gas sensor 105 detects that a concentration of any type of gas is greater than or equal to a preset value, the server 2 determines that the bathroom 1 is not clean. When the gas sensor 105 detects that a concentration of all detected types of gas is less than the preset value, the server 2 determines that the bathroom 1 is clean. The gas sensor 105 may be a semiconductor gas sensor, an infrared absorption gas sensor, an electrochemical sensor, an intelligent gas sensor, or the like.

At block S2, the second sensor 111 detects whether the door of the bathroom 1 is closed, and sends the second detection result to the server 2.

In one embodiment, the second sensor 111 may be a proximity sensor mounted in the switch 110. When the door of the bathroom 1 is closed, the switch 110 is in a closed state, at which time the proximity sensor is blocked by the switch 110, and a distance detected by the proximity sensor is less than or equal to a preset distance. When the door is opened, the switch 110 is in an open state, and the proximity sensor is not blocked by the switch 110, so that the distance detected by the proximity sensor is greater than the preset distance. The second sensor 111 sends the detected distance to the server 2, and the server 2 compares the detected distance with the preset distance to determine whether the door of the bathroom 1 is closed.

At block S3, the third sensor 301 detects the usage of the toilet paper on the roller 12 and sends the third detection result to the server 2.

The third sensor 301 may be a weight sensor or a proximity sensor. The weight sensor detects a weight of the toilet paper. The weight sensor transmits the detected weight of the toilet paper to the server 2, and the server 2 controls the indicator light 302 to indicate the usage of the toilet paper according to the detected weight of the toilet paper. The proximity sensor sends the detected distance between the roller holding portion 32 and the cover plate 33 to the server 2, and the server 2 controls the indicator light 302 to indicate the usage of the toilet paper according to the detected distance between the roller holding portion 32 and the cover plate 33.

At block S4, the server 2 receives the first detection result, the second detection result, and the third detection result.

At block S5, the server 2 further analyzes the first detection result, the second detection result, and the third detection result to obtain an analysis result, and performs a related operation according to the analysis result.

When the analysis result indicates that the smart toilet 10 is in a clean state, the door of the bathroom 1 is in an open state, and the amount of toilet paper on the roller 12 is sufficient, the server 2 sends a message to the mobile terminal 3 to remind the user that the bathroom 1 is not occupied with confidence.

When the analysis result indicates that the door of the bathroom 1 is in a closed state, regardless of whether the smart toilet 10 is in a clean state and whether the amount of toilet paper on the roller 12 is sufficient, the server 2 sends a message to the mobile terminal 3 that the bathroom 1 is currently occupied.

When the analysis result indicates that the smart toilet 10 is in an unclean state and the door of the bathroom 1 is in an open state, regardless of whether the amount of toilet paper on the roller 12 is sufficient, the server 2 sends a message to the mobile terminal 3 of cleaning personnel to clean the bathroom 1.

When the analysis result indicates that the smart toilet 10 is in an unclean state, regardless of whether the door of the bathroom 1 is in an open state, the server 2 controls the smart toilet 10 to perform automatic flushing and deodorization.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. A smart control system for monitoring a bathroom, the smart control system comprising:
    a server;
    a smart toilet mounted in the bathroom;
    a smart door handle mounted on a door of the bathroom; and
    a roller mounted in the bathroom and configured to hold toilet paper; wherein:
    the smart toilet comprises a first sensor configured to detect whether the smart toilet is clean and send a first detection result to the server;
    the smart door handle comprises a second sensor configured to detect whether the door of the bathroom is in an open state or a closed state and send a second detection result to the server;
    the roller comprises a third sensor configured to detect a usage of the toilet paper on the roller and send a third detection result to the server;
    the server analyzes the first detection result, the second detection result, and the third detection result to obtain an analysis result; and
    the server performs corresponding operations according to the analysis result.

2. The smart control system of claim 1, wherein:
    when the analysis result indicates that the smart toilet is in a clean state, the door of the bathroom is in the open state, and an amount of toilet paper on the roller is sufficient, the server sends a message to a mobile terminal to indicate that the bathroom is not occupied;
    when the analysis result indicates that the door of the bathroom is in the closed state, regardless of whether the smart toilet is in a clean state and whether the amount of toilet paper on the roller is sufficient, the server sends a message to the mobile terminal to indicate that the bathroom is currently occupied;
    when the analysis result indicates that the smart toilet is in an unclean state and the door of the bathroom is in the open state, regardless of whether the amount of toilet paper on the roller is sufficient, the server sends a message to the mobile terminal to indicate that the bathroom needs to be cleaned.

3. The smart control system of claim 1, wherein:
    when the analysis result indicates that the smart toilet is in an unclean state, regardless of whether the door of the bathroom is in the open state, the server controls the smart toilet to perform automatic flushing and deodorization.

4. The smart control system of claim 1, wherein:
    the first sensor comprises a camera and a gas sensor;
    the second sensor comprises a proximity sensor; and
    the third sensor comprises a weight sensor or a proximity sensor.

5. The smart control system of claim 1 further comprising an indicator light mounted on the smart door handle, wherein:
    when the analysis result indicates that an amount of toilet paper on the roller is sufficient and the door of the bathroom is in the open state, the indicator light displays a first color;
    when the analysis result indicates that the amount of toilet paper on the roller is less than sufficient and the door of the bathroom is in the open state, the indicator light displays a second color;
    when the analysis result indicates that the door of the bathroom is in the closed state, regardless of the amount of toilet paper on the roller, the indicator light displays a third color.

6. A smart control method for monitoring a bathroom, the smart control method comprising:
    detecting whether a smart toilet mounted in the bathroom is clean and generating a first detection result;
    detecting whether a door of the bathroom comprising a smart door handle mounted on an outer side of the door is in an open state or a closed state and generating a second detection result;
    detecting a usage of toilet paper on a roller mounted in the bathroom and generating a third detection result;
    analyzing the first detection result, the second detection result, and the third detection result to obtain an analysis result; and
    performing corresponding operations according to the analysis results.

7. The smart control method of claim 6 further comprising:
    sending a message to a mobile terminal, when the analysis result indicates that the smart toilet is in a clean state, the door of the bathroom is in the open state, and an amount of toilet paper on the roller is sufficient, to indicate that the bathroom is not occupied;
    sending a message to the mobile terminal, when the analysis result indicates that the door of the bathroom is in the closed state, regardless of whether the smart toilet is in a clean state and whether the amount of toilet paper on the roller is sufficient, to indicate that the bathroom is currently occupied;

sending a message to the mobile terminal, when the analysis result indicates that the smart toilet is in an unclean state and the door of the bathroom is in the open state, regardless of whether the amount of toilet paper on the roller is sufficient, to indicate that the bathroom needs to be cleaned.

8. The smart control method of claim 6 further comprising:

controlling the smart toilet, when the analysis result indicates that the smart toilet is in an unclean state, regardless of whether the door of the bathroom is in the open state, to perform automatic flushing and deodorization.

9. The smart control method of claim 6 further comprising:

displaying, by an indicator light when the analysis result indicates that an amount of toilet paper on the roller is sufficient and the door of the bathroom is in the open state, a first color;

displaying, by the indicator light when the analysis result indicates that the amount of toilet paper on the roller is less than sufficient and the door of the bathroom is in the open state, a second color;

displaying, by the indicator light when the analysis result indicates that the door of the bathroom is in the closed state, regardless of the amount of toilet paper on the roller, a third color.

\* \* \* \* \*